United States Patent [19]

Sweed

[11] 4,455,283

[45] Jun. 19, 1984

[54] MOLYBDENUM EPOXIDATION CATALYST RECOVERY

[75] Inventor: Norman H. Sweed, Berkeley Heights, N.J.

[73] Assignee: Atlantic Richfield Company, Los Angeles, Calif.

[21] Appl. No.: 381,120

[22] Filed: May 24, 1982

[51] Int. Cl.$^3$ .............................................. C01G 39/00
[52] U.S. Cl. ...................................... 423/53; 423/59; 502/56
[58] Field of Search ................ 423/53, 59; 252/411 R

[56] References Cited

U.S. PATENT DOCUMENTS

| 1,426,602 | 8/1922 | Robertson | 423/59 |
| 3,453,068 | 7/1969 | Taue | 423/59 |
| 3,819,663 | 6/1974 | Levine et al. | |

OTHER PUBLICATIONS

McCabe et al., "Unit Operations of Chemical Engineering", 1967, McGraw-Hill Book Co., N.Y., pp. 439–442.
Perry, "Chemical Engineers' Handbook", McGraw-Hill Book Co., N.Y., pp. 11–24 to 11–29, 11–35 to 11–36.

Primary Examiner—Herbert T. Carter
Attorney, Agent, or Firm—Craig E. Larson

[57] ABSTRACT

A process for recovering molybdenum values from a spent catalyst solution obtained from a crude reaction product of a molybdenum catalyzed epoxidation of an olefin with an organic hydroperoxide from which crude reaction product epoxide and alcohol corresponding to the hydroperoxide is removed, which process comprises vacuum evaporation without suppressed vaporization of the spent catalyst solution feed.

5 Claims, No Drawings

MOLYBDENUM EPOXIDATION CATALYST RECOVERY

BACKGROUND OF THE INVENTION

1. Field of the Invention

The present invention is concerned with the recovery and recycle of molybdenum catalyst values from distillation residues obtained in the process of epoxidizing olefinic compounds with organic hydroperoxides in the presence of liquid solutions of dissolved molybdenum. This invention is particularly concerned with evaporative techniques for concentrating such molybdenum values.

2. Description of the Prior Art

Oxirane compounds such as ethylene oxide, propylene oxide, and their higher homologs are valuable articles of commerce. One of the most attractive processes for synthesis of those oxirane compounds is described by Kollar in U.S. Pat. No. 3,351,635. According to Kollar, the oxirane compound (e.g., propylene oxide) may be prepared by epoxidation of an olefinically unsaturated compound (e.g., propylene) by use of an organic hydroperoxide and a suitable catalyst such as molybdenum.

During the epoxidation reaction the hydroperoxide is converted almost quantitatively to the corresponding alcohol. That alcohol may be recovered as a coproduct with the oxirane compound. However, it is the oxirane which is of primary concern.

Kollar teaches that oxirane compounds may be prepared from a wide variety of olefins. Lower olefins having three or four carbon atoms in an aliphatic chain are advantageously epoxidized by the process. The class of olefins commonly termed alpha olefins or primary olefins are epoxidized in a particularly efficient manner by the process. It is known to those in the art that primary olefins, e.g., propylene, butene-1, decene-1, hexadecene-1 etc., are much more difficulty epoxidized than other forms of olefins, excluding only ethylene. Other forms of olefins which are much more easily epoxidized are substituted olefins, alkenes with internal unsaturation, cycloalkenes and the like. Kollar teaches that notwithstanding the relative difficulty in epoxidizing primary olefins, epoxidation proceeds more efficiently when molybdenum, titanium or tungsten catalysts are used. Molybdenum is of special interest. Kollar teaches that activity of those metals for epoxidation of the primary olefins is surprisingly high and can lead to high selectivity of propylene to propylene oxide. These high selectivities are obtained at high conversions of hydroperoxide (50% or higher) which conversion levels are important for commercial utilization of the technology.

Kollar's epoxidation reaction proceeds under pressure in the liquid state and, accordingly, a liquid solution of the metal catalyst is preferred. Preparation of suitable catalysts is taught in U.S. Pat. Nos. 3,434,975; 3,453,218; and 3,480,563. It has been found that such suitable catalysts comprise high molecular weight, highly complex molybdenum compounds which, because of their low volatility, are carried through the process steps used to recover and separate unreacted olefin, the alkylene oxide product and the by-product alcohol resulting from the reduction of the organic hydroperoxide.

When an olefin is epoxidized with an organic hydroperoxide in the presence of molybdenum-containing catalyst according to the Kollar process, a product mixture containing unreacted olefin, alkylene oxide, an alcohol corresponding to the organic hydroperoxide and molybdenum catalyst is obtained. This product mixture is subjected to a series of distillations in order to resolve it into separate streams comprising unreacted olefin, which may be recycled to the epoxidation zone, and substantially pure alkylene oxide and alcohol products. The distillation residue (hereafter "TBA bottoms") contains spent molybdenum catalyst, some alcohol, acids as well as high boiling organic residues.

After the separation of valuable products of the reaction, it is desirable (both from economic and ecologic standpoints) that the catalyst be recovered from the remaining organic distillation residue. This residue contains substantially all of the catalyst withdrawn in the product mixture from the epoxidation zone. The residue stream (which usually contains from about 0.1 to about 1.0 wt. % molybdenum) can be recycled directly to the epoxidation zone (as suggested in the Kollar patent cited above), but direct recycle results in a buildup within the system of impurities (e.g., acids) which are deleterious to subsequent epoxidation reactions. Moreover, disposal of the residue stream (or a portion thereof, as in the case of a purge stream from direct recycle) presents substantial pollution problems. Accordingly, various methods have been proposed for the removal and recovery of molybdenum values from the distillation residue.

It is known that molybdenum catalyst may be recovered from the distillation residue by extraction with various aqueous mediums. For example, Khuri (U.S. Pat. No. 3,763,303) suggests liquid/liquid extraction of residue with an extractant consisting essentially of water, recovering the molybdenum-containing aqueous extract, evaporating the extract, calcining the solid obtained in the extract evaporation step, and recovering molybdenum values as molybdenum trioxide. The molybdenum trioxide is insoluble in epoxidation zone reaction mediums and, accordingly, must be redissolved prior to reuse as an epoxidation catalyst. Khuri also teaches use of acids or bases as the extracting agent, converting molybdenum into a recoverable compound of the acid or base.

British Patent Specification No. 1,317,480 discloses a recovery process involving extraction of spent epoxidation catalyst solutions with water or aqueous ammonia and recovery of molybdenum values from the aqueous extract either by precipitating molybdenum therefrom as a phosphomolybdate or by distillative stripping of volatile organics and water.

Commonly-assigned U.S. patent application Ser. No. 226,967, filed Jan. 21, 1981, teaches a further improved extraction method for the recovery of molybdenum which method comprises extraction of distillation residues (e.g., TBA bottoms) with water (without an added acid or base) and a water-immiscible organic solvent for the organic residue. The aqueous extract solution phase which is obtained contains mostly water but also contains dissolved molybdenum values and may contain low molecular weight organic material from the "spent catalyst solution". Higher molecular weight organic materials remain in the organic extract phase.

Commonly-assigned U.S. patent application Ser. No. 226,969, filed Jan. 21, 1981, teaches that when distillation residues (e.g., TBA bottoms) are subjected to aqueous extraction as taught by either the British patent (supra) or U.S. patent application Ser. No. 226,967, active molybdenum catalyst may be prepared from the extract by stripping off water and lower molecular weight organic materials. The '969 application further teaches that the product obtained by wiped film evaporation of distillation residues is a suitable material for use in the extraction/reuse procedure disclosed therein.

Wiped film evaporation of distillation residues is disclosed in Levine (U.S. Pat. No. 3,819,663). According to Levine, customary and regular procedures cannot be employed to resolve this material in view of the tendency of the molybdenum-containing residue to cake, coat and block conventional apparatus. Levine further teaches that wiped film evaporation removes volatile materials including most of the acidic compounds which are deleterious in the epoxidation zone. Hence, the wiped film evaporation residue may desirably be recycled to the epoxidation zone to satisfy catalyst requirements. In one embodiment of the Levine method, distillation residue is rapidly heated to a bottoms temperature of 375°–450° F. (190°–232° C.) at essentially atmospheric pressure in an agitated (or wiped) film evaporator to separate about 60 to 85 wt. % of the charge as vapor. The residue resulting may be reused as a liquid in an epoxidation reaction or, in another embodiment, may be further concentrated in a second agitated film evaporator having a scraping means to recover a solid residue. The solids obtained in this latter embodiment may be redissolved and reused in an epoxidation reaction. In addition to providing a readily reusable catalyst stream, the method of Levine produces volatile organic materials which are essentially free of metal residues and thus can be employed directly in furnaces as a non-fouling fuel.

Wiped (or agitated) film evaporation is a modified form of falling film evaporation employing a heating surface consisting of one relatively large diameter, jacketed tube containing an internal agitator. Feed enters at the top of the jacketed section and is spread out into a thin, highly turbulent film by the blades of the agitator. Concentrate is removed from the bottom of the jacketed section. Vapors are generally removed at the top of the unit. The technique is particularly suited for viscous heat-sensitive materials, providing very small hold-up volumes and residence times to reach desired end concentrations. Disadvantages of the technique are high cost, internal moving parts in the apparatus which may require considerable maintenance, and the small capacity of individual units.

Thus, while Levine represents an important advance with respect to molybdenum recovery from distillation residues obtained in the process of epoxidizing olefinic compounds with organic hydroperoxides in the presence of liquid solutions of dissolved molybdenum, further improvements in the evaporative concentration technique are desirable. A particular problem addressed by the present invention is the capacity restrictions imposed by the wiped film evaporators of Levine.

Thus, an object of this invention is to provide a method for the recovery of molybdenum from such distillation residues. More specifically, an object of this invention is an improved evaporative method which may be used alone, or in combination with other known methods for the said recovery of molybdenum.

Another object of this invention is to provide a method whereby molybdenum is recovered as an active, high quality catalyst for the hydroperoxide oxidation of olefins.

SUMMARY OF THE INVENTION

It has now been discovered that an active epoxidation catalyst can be obtained from spent epoxidation catalyst solutions, without fouling evaporative concentration equipment, by evaporating the solution in an evaporation means comprising a vapor-liquid separator and a heating means. The improved evaporative technique of this invention requires: (1) evaporation under vacuum pressures and (2) introduction of spent catalyst solution feed into the vapor-liquid separator of the evaporation means. This latter requirement—direct introduction of feed into the vapor-liquid separator—is a critical element of the present invention. On the one hand, preheating the feedstream in a suppressed vaporization heat exchanger promotes fouling of evaporative concentration equipment, even though vacuum conditions are employed. On the other hand, evaporating the spent catalyst solution under vacuum and without "suppressed vaporization" of the feed stream effectively eliminates fouling of the evaporative concentration equipment.

This absence of fouling is surprising in view of Levine U.S. Pat. No. 3,819,663 since Levine suggests that low hold-up volumes (or residence times) are necessary to avoid evaporator fouling. Temperatures employed in the method of this invention are in the same range as those employed by Levine and are well into the range where molybdenum precipitation from spent catalyst solutions has been found to occur. It has now been discovered that, if the two criteria mentioned above are fulfilled (vacuum operation and absence of suppressed feed vaporization), hold-up volume has no effect on evaporator operation with respect to fouling or solids formation.

While not wishing to be bound by any particular theory of operability, it appears that water present in the residue feed or formed as a result of alcohol dehydration at evaporation temperatures acts as a precipitating agent. Water may function by replacement of ligands in the coordination sphere of molybdenum with oxo groups, giving a new complex (or complexes) of greatly reduced solubility in an organic medium such as the residue feed of this invention:

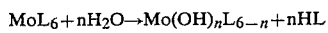

Catalyst values present in the concentrate recovered by the method of this invention can be recycled, with or without further treatment, to the epoxidation reactor.

According to the Levine patent, wiped film equipment is employed to avoid fouling of evaporative concentration eqiupment. An important aspect of the present invention is the availability of less expensive, more conventional equipment to fulfill the objects of this invention.

DETAILED DESCRIPTION OF THE INVENTION

The term "spent catalyst solution" refers to solutions obtained from the crude reaction product of a hydroperoxide oxidation of olefins by first removing unreacted olefin (e.g., propylene), alkylene oxide (e.g., propylene oxide) and a major portion of the alcohol corresponding to the reduced hydroperoxide (e.g., tertiary butyl hydroperoxide) used in the epoxidation reaction which reaction may be according to the procedure of Kollar U.S. Pat. No. 3,351,635, the teachings of which are incorporated herein by reference in their entirety. Spent catalyst solution, apart from molybdenum compounds, contains some alcohol, acids and other low molecular weight oxygenated compounds. It is not subjected to any chemical treatment before being processed according to the present invention.

Concentration of spent catalyst solutions may be accomplished in a variety of equipment types, best exemplified by simple reboilers with external heat exchangers. The evaporator means comprises a vapor-liquid separator and a heating means. It is essential that spent catalyst feed be introduced into the vapor-liquid separator to avoid suppressed vaporization of the feed stream. The feed must not be preheated in a suppressed vaporization heat exchanger. This direct feed introduction to the vapor-liquid separator allows water present in the feed or formed as a result of alcohol dehydration to immediately flash from the liquid mixture.

The evaporation equipment can be staged or single units. The units may be operated batch, semi-batch, continuous-batch, or continuously. Care should be taken to avoid short circuiting in the evaporation eqiupment.

As noted above, hold-up volume or residence time of product in the evaporator is not critical to avoid fouling. Therefore, the evaporator means is preferably a "circulation evaporator". This term refers to evaporators wherein a pool of liquid is held within the vapor-liquid separator; incoming feed mixes with liquid in the pool, rapidly stripping water present in the feed or formed as a result of alcohol dehydration; and liquid is circulated through a heat exchange means and back to the vapor-liquid separator to provide the sensible heat and heat of vaporization.

Pressures in the evaporator should generally be less than about 400 mm Hg. Higher pressures may suppress water vaporization, leading to fouling of the evaporation equipment. Preferably, pressures are within the range from about 1 to 200 mm Hg, more preferably within the range from about 25 to 75 mm Hg.

Evaporator temperatures are not especially critical to the method of this invention and are generally within the ranges suggested by the Levine patent. Temperatures should be within the range from about 180° C. to 250° C., preferably from about 200° C. to 250° C.

At sufficiently low pressures (e.g., 1 mm Hg), about 75% of the spent catalyst solution can be removed in a conventional reboiler. However, at these low pressures, an appreciable fraction of the distillate could by-pass a water-cooled condenser, requiring a refrigerated knock-back condenser to prevent loss of organics to the vacuum system. In a particularly preferred embodiment of this invention, spent catalyst solution is evaporated at a pressure of about 25 to 75 mm Hg and a temperature of about 200° C. to 220° C. for a time sufficient to recover 50 to 75 wt. % of the feed as overhead.

The concentrate recovered comprises molybdenum catalyst values and heavy organic residues. If desired, the concentrate may be subjected to further processing for the removal of the heavy organic residues. For example, see the method of U.S. patent application Ser. No. 226,967, filed Jan. 21, 1981, which is referred to in the Description of the Prior Art.

The following examples will serve to illustrate practice of the invention.

Example 1

Samples of a spent catalyst solution (containing about 3700 ppm Mo) were concentrated under vacuum at several temperature and pressure conditions in a rotary evaporator. The samples were obtained as the distillation bottoms resulting from the distillation of propylene oxide and tertiary butyl alcohol product produced by reaction of propylene with tertiary butyl hydroperoxide in the presence of a molybdenum containing catalyst as is described in Kollar U.S. Pat. No. 3,351,635. Evaporation conditions and results are shown in Table I. The results are expressed as the percentage of feed evaporated and the percentage of distillate which condensed using a 20° C. condenser. The uncondensed fraction was collected in a dry-ice-acetone-cooled trap. Some of the uncondensed material from the 20° C. condenser is due to the high vapor pressure of components of the mixture. However, a portion of the material remained uncondensed because the heat exchange area was too small. Therefore, the uncondensed fractions shown in Table I are higher than these that would be obtained in a system having a properly designed condenser. No solids formation was noted in any of the concentrates.

TABLE I

| Run | Sample | Temperature (°C.) | Pressure (mm Hg) | Run Time min. | % Feed Evaporated | % Distillate Condensed at 20° C. |
|---|---|---|---|---|---|---|
| 1[a] | A | 200 | 1 | 6 | 75 | 66 |
| 2 | A | 200 | 10 | 30 | 68 | 85 |
| 3 | A | 300 | 12 | 6 | 69 | 87 |
| 4 | A | 200 | 30 | 6 | 67 | 96 |
| 5 | A | 200 | 50 | 6 | 65 | >99 |
| 6[b] | A | 200 | 50 | 6 | 66 | 98 |
| 7 | A | 200 | 50 | 30 | 67 | >99 |
| 8 | A | 218 | 50 | 30 | 70 | >99 |
| 9 | A | 187 | 10 | 6 | 68 | 74 |
| 10 | A | 182 | 30 | 6 | 63 | 92 |
| 11 | B | 220 | 50 | 30 | 62 | >99 |
| 12 | B | 245 | 50 | 45 | 68 | — |

[a]The concentrate produced in this run flows freely at 200° C., but is very viscous at 25° C. The warm residue is readily soluble in tertiary butyl alcohol.
[b]The concentrate produced in this run flows well at 200° C., but is a sticky, tar-like solid at 25° C. The warm residue is readily soluble in tertiary butyl alcohol.

Two-thirds of the distillation residue is easily evaporated at pressures in the range of 50 mm Hg. Lowering pressures marginally increased evaporation: up to 75% of the feed was evaporated at 1 mm Hg (Run 1). The length of the runs had little effect on the percentage distilled. Compare runs 2 and 3 and runs 6 and 7. The fact that no solids formed in the concentrate produced in any of the runs indicates that evaporator residence times do not effect solids formation in open distillation systems of the type employed in this example. Furthermore, the relatively high evaporation temperature of run 12 (245° C.) indicates that temperature is not a critical parameter with respect to solids formation in open evaporation system operated under vacuum pressures.

Mo analyses of feed, distillate and bottoms from Runs 11 and 12 are shown in Table II.

TABLE II

|  | Feed | Distillate | Bottoms |
|---|---|---|---|
| Run 11 (220° C., 50 mm Hg, 30 min.) | | | |
| Mass | 100 | 70.1 | 29.9 |
| Mo (ppm) | 3681 | 3 | 15,000 |
| Run 12 (245° C., 50 mm Hg, 45 min.) | | | |
| Mass | 100 | 67.9 | 32.1 |
| Mo (ppm) | 3681 | 5.3 | 12,000 |

Example 2

To test how the concentrated Mo produced by the method of this invention performs when recycled to an epoxidation reactor, concentrate from run 1 of Example I (75% feed evaporated) was used to catalyze a batch epoxidation of propylene with tertiary butyl hydroperoxide. The results were compared with a similar test employing concentrate (80% of feed evaporated) produced in a wiped film evaporator operated under about atmospheric pressure and in accordance with Levine U.S. Pat. No. 3,819,663. The activities and selectivities of the catalysts were nearly identical.

Example 3

To determine whether conditions encountered in the rotary evaporator employed in Example 1 produce results which differ from those produced by conditions encountered in an otherwise identical, "non-rotary" evaporation zone, a sample of spent catalyst solution was evaporated in a round-bottom flask at 220° C. and 50 mm Hg. The pot temperature increased to 212° C. during the first hour as lights distilled off. During the next hour, the temperature rose to and remained at 220° C., effectively "cooking" the concentrate for an hour at high temperature. No solids were observed in the concentrate. The warm residue was readily soluble in tertiary butyl alcohol. About 73% of the residue feed was removed as distillate.

What is claimed is:

1. A process for the recovery of molybdenum from a reaction mixture obtained from the epoxidation of an olefin with an organic hydroperoxide in the presence of a molybdenum compound catalyst wherein product epoxide and the alcohol corresponding to the hydroperoxide are removed from the reaction mixture leaving a spent catalyst solution containing between about 0.1 and 2% molybdenum which process comprises evaporating the spent catalyst solution at a pressure less than 400 mm Hg in a circulation evaporator comprising a vapor-liquid separator and a heating means wherein spent catalyst solution is introduced to the vapor-liquid separator and recovering a concentrate comprising molybdenum catalyst values and heavy organic residues.

2. The process of claim 1 wherein the pressure is within the range from about 1 to 200 mm Hg.

3. The process of claim 1 wherein the pressure is within the range from about 25 to 75 mm Hg.

4. The process of claim 1 or claim 3 wherein the spent catalyst solution is evaporated at a temperature within the range from about 180° C. to 250° C. until 50 to 75 wt. % of the solution is evaporated overhead.

5. The processes of claim 4 wherein the temperature is within the range from about 200° C. to 220° C.

* * * * *